United States Patent
Hiruma et al.

(10) Patent No.: US 12,343,418 B2
(45) Date of Patent: Jul. 1, 2025

(54) HAIR COSMETIC

(71) Applicant: KAO CORPORATION, Tokyo (JP)

(72) Inventors: Daisuke Hiruma, Kita-ku (JP);
Mitsuki Takebayashi, Koshigaya (JP)

(73) Assignee: KAO CORPORATION, Tokyo (JP)

( * ) Notice: Subject to any disclaimer, the term of this patent is extended or adjusted under 35 U.S.C. 154(b) by 663 days.

(21) Appl. No.: 17/625,474

(22) PCT Filed: Jul. 1, 2020

(86) PCT No.: PCT/JP2020/025810
§ 371 (c)(1),
(2) Date: Jan. 7, 2022

(87) PCT Pub. No.: WO2021/006143
PCT Pub. Date: Jan. 14, 2021

(65) Prior Publication Data
US 2022/0280404 A1  Sep. 8, 2022

(30) Foreign Application Priority Data
Jul. 8, 2019  (JP) .................................. 2019-126744

(51) Int. Cl.
| | | |
|---|---|---|
| *A61K 8/46* | (2006.01) | |
| *A61K 8/22* | (2006.01) | |
| *A61K 8/41* | (2006.01) | |
| *A61Q 5/08* | (2006.01) | |
| *A61Q 5/10* | (2006.01) | |

(52) U.S. Cl.
CPC ................ *A61K 8/466* (2013.01); *A61K 8/22* (2013.01); *A61K 8/411* (2013.01); *A61Q 5/08* (2013.01); *A61Q 5/10* (2013.01)

(58) Field of Classification Search
CPC .......... A61K 8/466; A61K 8/22; A61K 8/411; A61Q 5/08; A61Q 5/10
See application file for complete search history.

(56) References Cited

U.S. PATENT DOCUMENTS

| | | |
|---|---|---|
| 5,627,149 A | 5/1997 | Patel et al. |
| 5,683,685 A | 11/1997 | Hirano et al. |
| 2009/0048132 A1 | 2/2009 | Paul et al. |
| 2010/0229314 A1 | 9/2010 | Takiguchi |
| 2011/0150804 A1 | 6/2011 | Nojiri et al. |
| 2013/0121946 A1 | 5/2013 | Randall et al. |
| 2013/0123161 A1 | 5/2013 | Randall et al. |
| 2014/0144456 A1 | 5/2014 | Hirahara et al. |
| 2021/0069081 A1 | 3/2021 | Hiruma et al. |

FOREIGN PATENT DOCUMENTS

| | | |
|---|---|---|
| CN | 1135329 A | 11/1996 |
| CN | 101411676 A | 4/2009 |
| CN | 103917221 A | 7/2014 |
| EP | 1 428 497 A1 | 6/2004 |
| EP | 2 201 931 A1 | 6/2010 |
| EP | 3 741 352 A1 | 11/2020 |
| JP | 8-198732 A | 8/1996 |
| JP | 2004-189745 A | 7/2004 |
| JP | 2004-323423 A | 11/2004 |
| JP | 2006-282616 A | 10/2006 |
| JP | 2009-108052 A | 5/2009 |
| JP | 2009-256277 A | 11/2009 |
| JP | 2010-65022 A | 3/2010 |
| JP | 2011-157312 A | 8/2011 |
| JP | 2019-123710 A | 7/2019 |
| WO | WO 95/20375 A1 | 8/1995 |
| WO | WO 2012/150709 A1 | 11/2012 |

OTHER PUBLICATIONS

Extended European Search Report issued Jun. 19, 2023 in European Patent Application No. 20837693.9, 7 pages.
International Search Report mailed on Sep. 8, 2020 in PCT/JP2020/025810 filed on Jul. 1, 2020 (3 pages).

*Primary Examiner* — Shirley V Gembeh
(74) *Attorney, Agent, or Firm* — Oblon, McClelland, Maier & Neustadt, L.L.P.

(57) ABSTRACT

A hair cosmetic containing the following components (A) and (B), wherein a mass ratio of the component (B) to the component (A), (B)/(A), is 0.25 or more and 1.90 or less:
(A) an aromatic sulfonic acid or a salt thereof having a molecular weight of 300 or less; and
(B) a cationic polymer having a cationic charge density of 3.3 meq/g or more and less than 4.5 meq/g.

17 Claims, No Drawings

HAIR COSMETIC

FIELD OF THE INVENTION

The present invention relates to a hair cosmetic.

BACKGROUND OF THE INVENTION

Hair is known to be damaged by chemical treatments such as hair coloring and permanent waving, which results in the deterioration of the feel such as stiffening when touched. In particular, this deterioration of the feel is noticeable in Asians' distinctive thick hair. Furthermore, damaged hair is affected by daily actions such as shampoo and blow-drying, which lead to the progress of denaturation, swelling, and loss of proteins in the hair. As a result, kinky and frizzy hair strongly develop, leading to deterioration of the feel such as poofy hair, irregular shape, or the hair dryness and tangles caused thereby. In addition, the deterioration of hair evenness and the decrease in manageability associated thereto evoke to the user a further sense of damage.

The hair cosmetics currently mainly used to reduce the effects of the damages as described above include emulsified products such as hair cream types containing waxes, higher alcohols, surfactants, and the like in order to impart manageability to the hair and prevent hair dryness, or gels containing a film-forming polymer (setting polymer). However, while such hair cosmetics can apply fat/oil and polymers to the surface of the hair to temporarily solve issues such as poor manageability and hair dryness, they cannot substantially improve the gloss and manageability of the hair.

On the other hand, hair cosmetics containing a specific organic acid, a specific organic solvent, and a specific di- or tri-peptide are known to be excellent in the effect of imparting hair manageability and feel, and the effect of preventing hair dryness (see Patent Literature 1). In addition, hair treatment agent compositions containing an organic solvent, a specific aromatic sulfonic acid, a specific surfactant, and an oil are known to be able to impart suppleness/body and a conditioning effect to the hair (see Patent Literature 2).

(Patent Literature 1) JP-A-2011-157312
(Patent Literature 2) JP-A-H08-198732

SUMMARY OF THE INVENTION

The present invention provides a hair cosmetic containing the following components (A) and (B), wherein the mass ratio of the component (B) to the component (A), (B)/(A), is 0.25 or more and 1.90 or less:
(A) an aromatic sulfonic acid or a salt thereof having a molecular weight of 300 or less; and
(B) a cationic polymer having a cationic charge density of 3.3 meq/g or more and less than 4.5 meq/g.

In addition, the present invention provides a hair bleaching or hair dyeing kit composed of
said hair cosmetic, and
a hair bleach or an oxidative hair dye comprising a first part containing an alkali agent and a second part containing an oxidizing agent.

Furthermore, the present invention provides use of said hair cosmetic as a pretreatment agent for a hair bleach or an oxidative hair dye comprising a first part containing an alkali agent and a second part containing an oxidizing agent.

Furthermore, the present invention provides a method for bleaching or dyeing hair, comprising the following steps (i) and (ii):

(i) a step of applying said hair cosmetic to the hair; and
(ii) a step of applying a mixture of a first part containing an alkali agent and a second part containing an oxidizing agent of a hair bleach or an oxidative hair dye to the hair after the step (i).

DETAILED DESCRIPTION OF THE INVENTION

The hair cosmetic described in Patent Literature 1 exhibits an excellent hair improving effect, and is effective in imparting hair manageability and feel, preventing hair dryness, and further improving hair tip evenness and hair smoothness. However, the effect is reduced when the hair cosmetic is removed by a cleansing treatment such as shampooing, and a long-lasting effect of manageability could not be achieved. In addition, the hair treatment agent composition described in Patent Literature 2 could impart suppleness, body, and smoothness to the hair, but did not sufficiently improve the manageability reduced by hair damage.

Furthermore, the criteria of improving effect demanded by users in recent years are increasing year by year. In addition, due to changes in the social and living environment, the daily spare time is decreasing, and a need for obtaining a long-lasting effect with less effort is arising. For this reason, in recent years, conventional hair cosmetics has become insufficient to meet the criteria of users' demand.

Therefore, the present invention relates to a hair cosmetic having an excellent hair improving effect, which is able to reduce frizzy and poofy hair which occur naturally or after a chemical treatment such as hair dyeing, and to maintain the effect of hair manageability for a certain period of time, by a single treatment.

The present inventors found that it is possible to obtain a hair cosmetic having a high hair improving effect which satisfies the above needs by using an aromatic sulfonic acid and a cationic polymer having a specific charge density in combination at a certain ratio, and completed the present invention.

The hair treatment agent composition of the present invention can mitigate frizzy hair and reduce poofy hair, which occur naturally or after a chemical treatment such as hair dyeing, improve the manageability of hair, and furthermore, maintain the effect for a certain period of time by a single treatment.

[Component (A): Aromatic Sulfonic Acid or a Salt Thereof Having a Molecular Weight of 300 or Less]

Examples of the aromatic sulfonic acid or a salt thereof having a molecular weight of 300 or less, the component (A), include a benzenesulfonic acids, a naphthalenesulfonic acids, an azulenesulfonic acids, and a benzophenonesulfonic acids.

Examples of the benzenesulfonic acids include the compounds of the following formula (1):

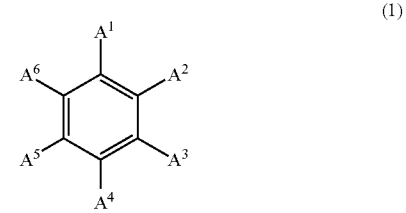

wherein one or more of $A^1$ to $A^6$ represents a sulfo group or a salt thereof, and the remainder represents a hydrogen atom or an alkyl group having 1 to 3 carbon atoms.

Specific examples of the benzenesulfonic acids include benzenesulfonic acid, o-toluenesulfonic acid, p-toluenesulfonic acid, xylenesulfonic acid, cumenesulfonic acid, ethylbenzenesulfonic acid, 2,4,6-trimethylbenzenesulfonic acid and the salts thereof.

Examples of the naphthalenesulfonic acids include the compounds of the following formula (2):

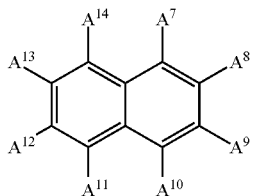

(2)

wherein one or more of $A^7$ to $A^{14}$ represents a sulfa group or a salt thereof, and the remainder represents a hydrogen atom, a halogen atom, a hydroxy group, a nitro group, a carboxy group, an alkoxycarbonyl group having 2 to 4 carbon atoms, an alkyl group having 1 to 3 carbon atoms, an alkoxy group having 1 to 3 carbon atoms, a formyl group, an alkenyl group having 2 or 3 carbon atoms, an acyl group having 2 or 3 carbon atoms, a phenylazo group optionally having a substituent or —N(R') (R") (R' and R" are a hydrogen atom, an alkyl group having 1 to 3 carbon atoms, an alkenyl group having 2 or 3 carbon atoms, a phenyl group, a benzyl group or an acyl group having 2 or 3 carbon atoms).

Specific examples of this naphthalenesulfonic acids include 1- or 2-naphthalenesulfonic acid (α- or β-naphthalenesulfonic acid), 2,7-naphthalenedisulfonic acid, 1,5-naphthalenedisulfonic acid, 2,6-naphthalenedisulfonic acid, 1-naphthol-2-sulfonic acid, 1-naphthol-4-sulfonic acid, 2-naphthol-6-sulfonic acid, 2-naphthol-7-sulfonic acid, 2,3-dihydroxynaphthalene-6-sulfonic acid, 1,7-dihydroxynaphthalene-3-sulfonic acid, J acid (2-amino-5-naphthol-7-sulfonic acid), 1-amino-2-naphthol-4-sulfonic acid, 1-naphthylamine-4-sulfonic acid, Broenner's acid (2-naphthylamine-6-sulfonic acid), Cleve's acid (1-naphthylamine-7-sulfonic acid), 2-naphthylamine-1-sulfonic acid, 1-naphthylamine-6-sulfonic acid, 1-naphthylamine-8-sulfonic acid, 2,7-diamino-1-naphthol-3-sulfonic acid, 7,8-diamino-1-naphthol-3-sulfonic acid, naphthalenesulfonic acid-formaldehyde polycondensate having a molecular weight of 300 or less, 6-methyl-2-naphthalenesulfonic acid, 4-ethyl-1-naphthalenesulfonic acid, 5-isopropyl-1-naphthalenesulfonic acid, 5-butyl-2-naphthalenesulfonic acid, and the salts thereof.

Specific examples of the azulenesulfonic acids include guaiazulenesulfonic acid, 1-azulenesulfonic acid, 3-acetyl-7-isopropyl-1-azulenesulfonic acid, 3-(2-hydroxyethyl)-7-isopropyl-1-azulenesulfonic acid, 3-methyl-7-isopropyl-1-azulenesulfonic acid, 7-isopropyl-1-azulenesulfonic acid, 1,4-dimethyl-7-isopropyl-2-azulenesulfonic acid, 1,3-azulenedisulfonic acid, 3-formyl-4,6,8-trimethyl-1-azulenesulfonic acid, and the salts thereof.

Examples of the benzophenonesulfonic acids include the compounds of the following formula (3):

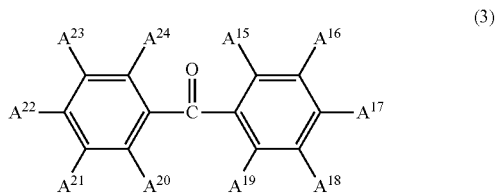

(3)

wherein one or more of $A^{15}$ to $A^{24}$ represents a sulfo group or a salt thereof, and the remainder represents a hydrogen atom, a halogen atom, a hydroxy group, a carboxy group, an amino group, an alkyl group having 1 to 3 carbon atoms, an alkoxy group having 1 to 3 carbon atoms, an alkenyl group having 2 or 3 carbon atoms, or an acyl group having 2 or 3 carbon atoms.

Specific examples of this benzophenonesulfonic acids include o-chlorobenzophenonesulfonic acid, p-chlorobenzophenonesulfonic acid, 2-hydroxybenzophenonesulfonic acid, 4-hydroxybenzophenonesulfonic acid, 2-aminobenzophenonesulfonic acid, 4-aminobenzophenonesulfonic acid, 2-methylbenzophenonesulfonic acid, 4-methoxybenzophenonesulfonic acid, 4,4'-dimethylbenzophenonesulfonic acid, and the salts thereof.

Examples of the salt of the above aromatic sulfonic acids include a sodium salt, a potassium salt, a lithium salt, an aluminum salt, an ammonium salt ($N_4^+$), and an organic ammonium salt.

The aromatic sulfonic acid or a salt thereof, the component (A), is preferably at least one selected from the group consisting of the benzenesulfonic acids of the formula (1), the naphthalenesulfonic acids of the formula (2), and the benzophenonesulfonic acids of the formula (3), and furthermore, more preferably at least one selected from the group consisting of p-toluenesulfonic acid, xylenesulfonic acid, 2-naphthalenesulfonic acid (β-naphthalenesulfonic acid), 1-naphthalenesulfonic acid (α-naphthalenesulfonic acid), and the salts thereof, from the viewpoint of mitigating frizzy hair, improving manageability, further strongly mitigating fuzzy hair, giving a soft feel, and preventing the hair from getting entangled, when combined with the component (B) at a specific ratio. Among these, p-toluenesulfonic acid or a salt thereof is still more preferable from the above viewpoint.

The aromatic sulfonic acid or a salt thereof can be used alone or two or more thereof can be used in combination. When combined with the component (B) at a specific ratio, the content of the component (A) in the hair cosmetic of the present invention is, from the viewpoint of mitigating frizzy hair and improving manageability, preferably 0.01 mass % or more, more preferably 0.05 mass % or more, still more preferably 0.10 mass % or more, still more preferably 0.20 mass % or more, still more preferably 0.50 mass % or more, still more preferably 0.70 mass % or more, still more preferably 0.80 mass % or more, still more preferably 0.9 mass % or more, and from the viewpoint of suppressing a change in viscosity over time which can occur due to a decrease in pH, preferably 5 mass % or less, more preferably 3.0 mass % or less, still more preferably 2.0 mass % or less, and still more preferably 1.8 mass % or less.

[Component (B): Cationic Polymer Having a Cationic Charge Density of 3.3 Meq/g or More and Less than 4.5 Meq/g]

Specific examples of the cationic polymer having a cationic charge density of 3.3 meq/g or more and less than 4.5 meq/g, the component (B), include N-methylvinylimidazolinium/vinylpyrrolidone copolymer (polyquaternium-16, for example, Luviquat Style (charge density: 3.57 meq/g); manufactured by BASF) and acrylamide/acrylic acid/dimethyldiallylammonium chloride copolymer solution (polyquaternium-39, for example, Merquat PLUS 3330 (charge density: 3.41 meq/g); manufactured by Lubrizol Advanced Materials). Of these, N-methylvinylimidazolinium/vinylpyrrolidone copolymer is preferable from the viewpoint of mitigating frizzy hair and improving manageability when combined with the component (A) at a specific ratio.

When combined with the component (A) at a specific ratio, the cationic charge density of the cationic polymer, the component (B), is, from the viewpoint of mitigating frizzy hair and improving manageability, preferably 3.4 meq/g or more, more preferably 3.45 meq/g or more, still more preferably 3.5 meq/g or more, and from the viewpoint of further reducing the friction feeling upon rinsing, preferably 4.0 meq/g or less, more preferably 3.7 meq/g or less.

The cationic polymer, the component (B), can be used alone or two or more thereof can be used in combination, and when combined with the component (A) at a specific ratio, the content in the hair cosmetic of the present invention is, from the viewpoint of mitigating frizzy hair and improving manageability, preferably 0.10 mass % or more, more preferably 0.25 mass % or more, still more preferably 0.30 mass % or more, still more preferably 0.6 mass % or more, still more preferably 0.8 mass % or more, still more preferably 1.0 mass % or more, and from the viewpoint of suppressing stickiness of the hair after finish and improving the stability of the composition, preferably 20 mass % or less, more preferably 10 mass % or less, still more preferably 5 mass % or less, still more preferably 3.0 mass % or less, still more preferably 2.5 mass % or less, still more preferably 2.0 mass % or less, still more preferably 1.9 mass % or less.

Moreover, the mass ratio of the component (B) to the component (A), (B)/(A), is 0.25 or more, preferably 0.30 or more, more preferably 0.50 or more, still more preferably 0.55 or more, still more preferably 0.60 or more, still more preferably 0.8 or more, still more preferably 1.0 or more, and 1.90 or less, preferably 1.85 or less, more preferably 1.8 or less, from the viewpoint of mitigating frizzy hair and improving manageability. It was found that when the component (A) and the component (B) are mixed within the above mass ratio range, an adhering, soft and robust film is formed. Therefore, it can be considered that by applying to the hair a hair cosmetic containing the component (A) and the component (B) within the above mass ratio range, a film having the above physical characteristics is formed on the surface of the hair, and an effect of mitigating frizzy hair and improving manageability is exhibited by the interaction between the hairs. In addition, it can be considered that by having a cationic charge density of the component (B) of 3.3 meq/g or more, the adsorptivity of the film to the hair surface is increased, it is not easily washed away by a cleanser, and a long-lasting manageability effect can be exhibited.

[Component (C): Glycylglycine Derivative of the Formula (4) or a Salt Thereof]

The hair cosmetic of the present invention preferably further contains the compound of the following formula (4) or a salt thereof as the component (C):

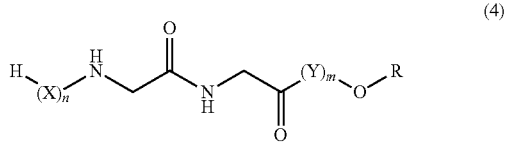

(4)

wherein X represents a divalent hydrocarbon group having 1 to 4 carbon atoms optionally substituted with a hydroxy group, or an amino acid residue, and Y represents an amino acid residue or a divalent group of the following chemical formula (5):

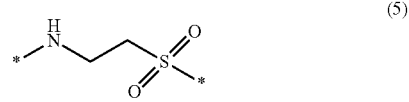 [SMILES: *NCCS(*)(=O)=O]

(5)

(wherein -* represents a bond which binds to an adjacent carbonyl group or oxygen atom.), R represents a monovalent hydrocarbon group having 1 to 4 carbon atoms optionally substituted with a hydrogen atom or a hydroxy group, and m and n represent 0 or 1, provided that when m and n are 1 at the same time, X is not an amino acid residue.

The component (C) is a glycylglycine derivative of the formula (4) or a salt thereof, but may be in a free form or an amphoteric ion. Examples of the salt of the glycylglycine derivative include an inorganic acid salt such as a hydrochloride or a sulfate; an organic acid salt such as a lactate; an ammonium salt such as an ammonium salt or an alkylammonium salt; and an alkali metal salt such as a sodium salt.

In the formula (4), the divalent hydrocarbon group having 1 to 4 carbon atoms optionally substituted with a hydroxy group, which is represented by X, may be saturated or unsaturated, and linear or branched, and of these, a divalent saturated hydrocarbon group substituted with a hydroxy group or a divalent saturated hydrocarbon group is preferable.

Examples of the divalent hydrocarbon group include a methylene group, an ethylene group, an ethylidene group, a vinylene group, a trimethylene group, an isopropylidene group, a 1-propenylene group, a tetramethylene group, a 2-methyltrimethylene group, a 1-methyltrimethylene group, and a 1-butenylene group.

Examples of the divalent hydrocarbon group substituted with a hydroxy group include a 1-hydroxyethylene group, a 1-hydroxytrimethylene group, a 1,2-dihydroxytrimethylene group, a 1-hydroxytetramethylene group, a 1,2-dihydroxytetramethylene group, a 1,3-dihydroxytetramethylene group, and a 1,2,3-trihydroxytetramethylene group.

In the formula (4), the "amino acid residue" represented by X means a unit amino acid moiety to form an oligopeptide, which can be obtained by synthesis, or can be derived from all the amino acids present in the living body, and may be a D-form or an L-form.

Examples of the amino acid residue represented by X include a basic amino acid residue such as an arginine residue, a lysine residue, and a histidine residue; an aliphatic amino acid residue such as an alanine residue and a glycine residue; an aromatic amino acid residue such as a phenylalanine residue, a tyrosine residue, and a tryptophan residue; an acid amide amino acid residue such as a glutamine residue and an asparagine residue; an acidic amino acid residue such as a glutamic acid residue, an aspartic acid residue, and a cysteic acid residue; a hydroxy amino acid residue such as a serine residue and a threonine residue; and a cyclic amino acid residue such as a proline residue, an N-methylproline residue, and a 4-hydroxyproline residue. Of these, an arginine residue, an alanine residue, a phenylalanine residue, a glycine residue, a glutamine residue, a glutamic acid residue, a serine residue, a proline residue, an N-methylproline residue, and a 4-hydroxyproline residue are preferable.

In the formula (4), examples of the amino acid residue represented by Y include the same as those of X above, but Y is preferably an arginine residue, an alanine residue, a glycine residue, a glutamine residue, a glutamic acid residue, a serine residue, a proline residue, a 4-hydroxyproline residue, or a divalent group represented by the above chemical formula (5).

In the formula (4), the monovalent hydrocarbon group having 1 to 4 carbon atoms optionally substituted with a hydroxy group, which is represented by R, may be saturated or unsaturated, and linear or branched. The monovalent hydrocarbon group is preferably an alkyl group, and examples thereof include a methyl group, an ethyl group, a propyl group, a butyl group, an isopropyl group, an isobutyl group, an s-butyl group, and a t-butyl group.

The monovalent hydrocarbon group substituted with a hydroxy group is preferably a hydroxyalkyl group, and examples thereof include a hydroxymethyl group, a 2-hydroxyethyl group, a 3-hydroxypropyl group, a 4-hydroxybutyl group, a 2,3-dihydroxyethyl group, a 2,3,4-trihydroxybutyl group, and a 2,4-dihydroxybutyl group.

Examples of suitable glycylglycine derivatives in the present invention include a compound of any of the formulas (G1) to (G10), and from the viewpoint of mitigating frizzy hair and improving manageability, a compound of any of the formulas (G3) to (G10) is more preferable, and a compound of any of the formulas (G9) and (G10) (glycylglycylglycine and glycylglycine) is particularly preferable. These glycylglycine derivatives may be in a free form or an amphoteric ion, and may form a salt. In addition, one of these can be used alone or two or more of these can be used in combination.

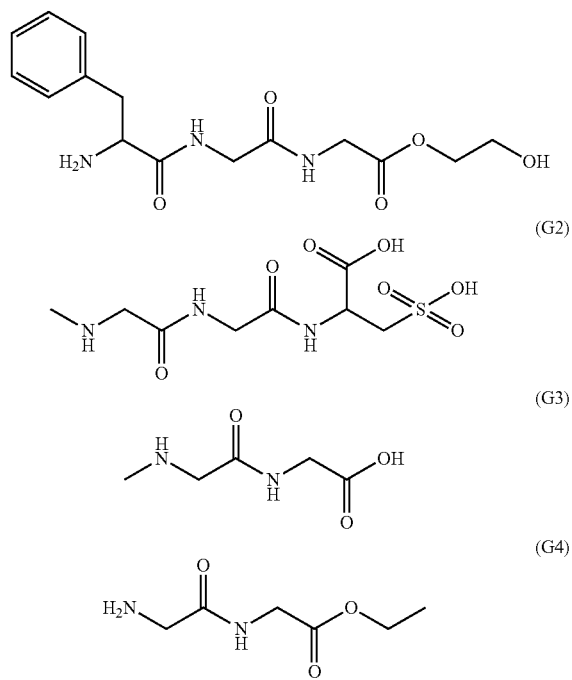

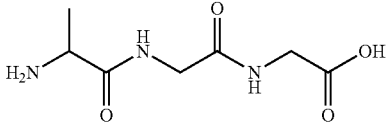

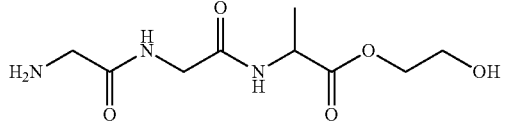

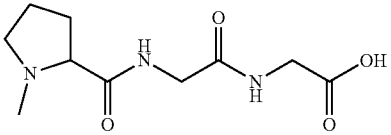

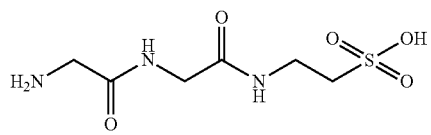

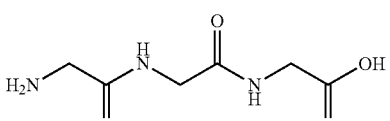

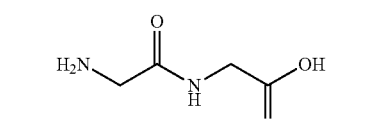

The content of the component (C) in the hair cosmetic of the present invention is, from the viewpoint of mitigating frizzy hair and improving manageability, and from the viewpoint of suppressing a change in viscosity over time when using a thickener which is sensitive to pH due to having a pH buffering ability, preferably 0.01 mass % or more, more preferably 0.05 mass % or more, still more preferably 0.1 mass % or more, still more preferably 0.3 mass % or more, still more preferably 0.5 mass % or more, and from the viewpoint of suppressing cost and suppressing the difficulty of adjusting the pH due to the pH buffering ability, preferably 10.0 mass % or less, more preferably 5.0 mass % or less, still more preferably 3.0 mass % or less, still more preferably 1.5 mass % or less, still more preferably 1.2 mass % or less, still more preferably 1.0 mass % or less.

The mass ratio of the component (C) to the total mass of the component (A) and the component (B) in the hair cosmetic of the present invention is, from the viewpoint of mitigating frizzy hair and improving manageability, preferably 0.1 or more, more preferably 0.2 or more, still more preferably 0.3 or more, still more preferably 0.4 or more, and from the viewpoint of suppressing cost and suppressing the difficulty of adjusting the pH due to the pH buffering ability, preferably 5 or less, more preferably 4 or less, still more preferably 3 or less, still more preferably 2 or less, still more preferably 1 or less.

[Medium]

The hair cosmetic of the present invention can contain water and/or an organic solvent as a medium, and preferably contains water from the viewpoint of solubility with the other components and economic efficiency. Examples of the organic solvent include a lower alkanol such as ethanol, 1-propanol, and 2-propanol; an aromatic alcohol such as benzyl alcohol and 2-benzyloxyethanol; a polyol such as ethylene glycol, diethylene glycol, triethylene glycol, polyethylene glycol, propylene glycol dipropylene glycol, polypropylene glycol, 1,2-butylene glycol, 1,3-butylene glycol, 1,4-butylene glycol, pentylene glycol, hexylene glycol, glycerol, diglycerol, and polyglycerol; an alkoxy alcohol such as ethoxyethanol, ethoxydiglycol, and methoxyethanol; an N-alkylpyrrolidone such as N-methylpyrrolidone and N-ethylpyrrolidone; an alkylene carbonate such as propylene carbonate; and a lactone such as γ-valerolactone and γ-caprolactone. In addition, from the viewpoint of viscosity stability over time, one or more selected from the group consisting of ethanol, propylene glycol, 1-propanol, 2-propanol, benzyl alcohol, polyethylene glycol, and glycerol is preferable, among which one or more selected from the group consisting of ethanol and propylene glycol is more preferable.

The content of water in the hair cosmetic of the present invention is, from the viewpoint of solubility with the other components and economic efficiency, preferably 45 mass % or more, more preferably 50 mass % or more, still more preferably 60 mass % or more, and from the viewpoint of easiness to dry, preferably 99 mass % or less, more preferably 95 mass % or less, still more preferably 90 mass % or less.

The organic solvent can be used alone or two or more thereof can be used in combination. The content of the organic solvent in the hair cosmetic of the present invention is, from the viewpoint of improving solubility with the other components, antiseptic properties, and viscosity stability, preferably 0.05 mass % or more, more preferably 0.1 mass % or more, still more preferably 0.5 mass % or more, still more preferably 1 mass % or more, still more preferably 3 mass % or more, still more preferably 5 mass % or more, and from the viewpoint of suppressing inflammability and irritation, preferably 30 mass % or less, more preferably 20 mass % or less, still more preferably 10 mass % or less.

[Thickener]

The hair cosmetic of the present invention can further contain a synthetic polymer compound, a semi-synthetic polymer compound or a natural polymer compound as a thickener from the viewpoint of enabling even application to the hair and adjusting the viscosity to avoid dripping. Examples of the synthetic polymer compound, semi-synthetic polymer compound, and natural polymer compound include a polyacrylic acid (for example, Carbopol 941 and 981; Lubrizol Advanced Materials), an acrylates/alkyl methacrylate copolymer (for example, Carbopol ETD2020; Lubrizol Advanced Materials), a (vinylpyrrolidone/dimethylaminoethyl methacrylate) copolymer (for example, Copolymer 845, Copolymer 937, and Copolymer 958; ISB Japan), methyl cellulose (for example, Metolose SM; Shin-Etsu Chemical), ethyl cellulose (for example, EMULFREE CBG; Ikeda Corporation), hydroxyethyl cellulose (for example, CELLOSIZE QP4400H and QP52000H; Dow Chemical Japan, SE-600, SE-850, and SE900; Daicel Chemical Industries), hydroxypropyl cellulose (for example, Nisso HPC-H and HPC-M; Nippon Soda), hydroxypropyl xanthan gum (for example, RHABALL GUM EX; Sumitomo Dainippon Pharma), Pullulan (for example, Pullulan PF-20 and Pullulan PI-20; Hayashibara), and xanthan gum (for example, ECHO GUM; Sumitomo Dainippon Pharma). From the viewpoint of having little impact on the other components, a nonionic polymer compound is preferable, among which one or more selected from the group consisting of hydroxyethyl cellulose, methyl cellulose, xanthan gum and hydroxypropyl xanthan gum is more preferable.

The thickener can be used alone or two or more thereof can be used in combination. The content of the thickener in the hair cosmetic of the present invention is, from the viewpoint of enabling even application to the hair and adjusting the viscosity to avoid dripping, preferably 0.05 mass % or more, more preferably 0.1 mass % or more, still more preferably 0.5 mass % or more, and preferably 20 mass % or less, more preferably 10 mass % or less, still more preferably 5 mass % or less.

[Surfactant]

The hair cosmetic of the present invention can contain a surfactant from the viewpoint of feel and solubility performance. As the surfactant, any of a cationic surfactant, a nonionic surfactant, an amphoteric surfactant, and an anionic surfactant can be used.

As the cationic surfactant, a mono long chain alkyl quaternary ammonium salt is preferable, and specific examples thereof include cetrimonium chloride, steartrimonium chloride, behentrimonium chloride, stearalkonium chloride, and benzalkonium chloride.

Examples of the nonionic surfactant include a polyoxyalkylene alkyl ether, a polyoxyalkylene alkenyl ether, a sucrose ester of higher fatty acid, a polyglycerol ester of fatty acid, a higher fatty acid mono- or di-ethanolamide, polyoxyethylene hydrogenated castor oil, a polyoxyethylene sorbitan fatty acid ester, a polyoxyethylene sorbitol fatty acid ester, an alkyl saccharide, an alkyl amine oxide, and an alkyl amidoamine oxide.

Examples of the amphoteric surfactant include imidazoline, carbobetaine, amido betaine, sulfobetaine, hydroxysulfobetaine, and amidosulfobetaine.

Examples of the anionic surfactant include an alkylbenzene sulfonate, an alkyl or alkenyl ether sulfate, an alkyl or alkenyl sulfate, an olefin sulfonate, an alkane sulfonate, a saturated or unsaturated fatty acid salt, an alkyl or alkenyl ether carboxylate, an α-sulfo fatty acid salt, an N-acyl amino acid, a phosphate mono- or di-ester, and a sulfosuccinic acid ester. Examples of the alkyl ether sulfate include a polyoxyethylene alkyl ether sulfate. Examples of the counterion of the anionic group of these anionic surfactants include an alkali metal ion such as a sodium ion and a potassium ion; an alkaline earth metal ion such as a calcium ion and a magnesium ion; an ammonium ion; and an alkanolamine having from 1 to 3 alkanol groups having 2 or 3 carbon atoms (for example, monoethanolamine, diethanolamine, triethanolamine, and triisopropanolamine).

These surfactant can be used alone or two or more thereof can be used in combination. The content of the surfactant in the hair cosmetic of the present invention is preferably 0.1 mass % or more, more preferably 0.2 mass % or more, still more preferably 0.5 mass % or more, and preferably 30 mass % or less, more preferably 20 mass % or less, still more preferably 15 mass % or less, from the viewpoint of feel and solubility performance.

[Other Optional Components]

Other components usually used as cosmetic raw materials can be further added to the hair cosmetic of the present invention as long as its stable liquid form and function as a hair cosmetic are not impaired. Examples of such optional components include a penetration promoter, a pearlescent agent, a preservative, a sequestering agent, a stabilizer, an antioxidant, an ultraviolet absorber, a moisturizing agent, and a perfuming agent, and specific examples of the optional component include a higher alcohol, a higher fatty acid, a fatty acid ester, a hydrocarbon oil, a silicone, a protein hydrolysate, a protein derivative, an amino acid, a plant extract, a vitamin, and a fragrance.

[pH]

The pH of the hair cosmetic of the present invention is, from the viewpoint of suppressing irritation, preferably 3.0 or more, more preferably 3.5 or more, still more preferably 4.0 or more, and from the viewpoint of suppressing irritation and long-term pH stability, preferably 6.0 or less, more preferably 5.0 or less.

Examples of the pH adjuster for adjusting the hair cosmetic to the above pH include an inorganic acid such as hydrochloric acid and phosphoric acid, an organic acid such as citric acid, glycolic acid, and lactic acid, a hydrochloride such as ammonium chloride and monoethanolamine hydrochloride, an acid such as a phosphate such as potassium dihydrogen phosphate and disodium hydrogen phosphate, an alkali metal hydroxide such as sodium hydroxide and potassium hydroxide, and a carbonate such as sodium carbonate, potassium carbonate, sodium bicarbonate, potassium bicarbonate, and guanidine carbonate.

[Viscosity]

The viscosity of the hair cosmetic of the present invention is, from the viewpoint of applicability to the hair and preventing dripping from the hands or hair, preferably 10 mPa·s or more, more preferably 50 mPa·s or more, still more preferably 100 mPa·s or more, and from the viewpoint of easiness to spread on the hair, preferably 4,000 mPa·s or less, more preferably 3,000 mPa·s or less, still more preferably 2,000 mPa·s or less. Here, in the present invention, the viscosity means the value after measuring at 30° C. using a B-type viscometer and rotating at 60 rpm for 1 minute. Note that for the rotor and rotation speed used for measurement, appropriate conditions are selected according to the manual and the like of the measuring device, based on the viscosity of the hair cosmetic.

[Form]

The form of the hair cosmetic of the present invention can be appropriately selected from liquid, gel, paste, cream, wax, and the like, but a liquid using water or a lower alcohol, particularly water, is preferable as the solvent.

[Method of Use]

The hair cosmetic of the present invention may be applied to dry hair or may be applied to wet hair, but it is preferable to apply it to dry hair from the viewpoint of mitigating frizzy hair, reducing poofy hair, and further improving the manageability and feel of the hair.

The amount of hair cosmetic to apply to the hair is, in terms of bath ratio to the mass of hair (mass of hair cosmetic/mass of hair), preferably 0.05 or more, more preferably 0.1 or more, still more preferably 0.2 or more, still more preferably 0.3 or more, and preferably 2.0 or less, more preferably 1.5 or less, still more preferably 1.0 or less, from the viewpoint of reducing poofy hair and further improving the manageability and feel of the hair. The hair to which the hair cosmetic is applied may be all or a part of the hair. For example, it is possible to reduce poofy hair and further improve the manageability and feel of the hair by applying the hair cosmetic to severely damaged hair tips.

To spread the hair cosmetic onto the whole hair after application to the hair, a method using the hands such as rubbing the hair cosmetic onto the hair or finger combing the hair; a method using a tool such as a brush, a comb, or a brush; a combination of both, and the like should be used.

After applying the hair cosmetic to the hair, it is preferable to leave the hair to which the hair cosmetic is applied for a certain period of time from the viewpoint of further improving the manageability and feel of the hair. The temperature upon leaving is preferably 15° C. or more, and preferably 100° C. or less, more preferably 60° C. or less, and still more preferably 30° C. or less. In terms of easily treating without requiring a special device when treating with the hair cosmetic, 15° C. or more and less than 30° C., that is, room temperature is preferable. On the other hand, from the viewpoint of further shortening the leaving time, it can be left while heating with a heater or the like, and the temperature in this case is preferably 30° C. or more, more preferably 40° C. or more, and preferably 100° C. or less, more preferably 60° C. or less.

The time for leaving the hair to which the hair cosmetic is applied is preferably 15 seconds or more, more preferably 30 seconds or more, still more preferably 1 minute or more, still more preferably 3 minutes or more, still more preferably 5 minutes or more, and preferably 60 minutes or less, more preferably 45 minutes or less, still more preferably 30 minutes or less, from the viewpoint of further improving the manageability and feel of the hair. When leaving while heating with a heater or the like as described above, the leaving time can be further shortened, and the leaving time in this case is preferably 15 seconds or more, more preferably 30 seconds or more, still more preferably 1 minute or more, still more preferably 3 minutes or more, still more preferably 5 minutes or more, and preferably 30 minutes or less, more preferably 15 minutes or less, still more preferably 10 minutes or less. After leaving the hair to which the hair cosmetic is applied for the above time, it is preferable not to rinse the hair cosmetic from the hair from the viewpoint of further improving the manageability and feel of the hair.

The hair cosmetic of the present invention is preferably used as a hair conditioning agent such as a hair treatment, or a hair styling agent, and in particular, is preferably used together with a hair bleach or an oxidative hair dye comprising a first part containing an alkali agent and a second part containing an oxidizing agent, from the viewpoint of mitigating frizzy hair, reducing poofy hair, which occur due to a chemical treatment of bleach or hair dyeing, and further improving the manageability of the hair. In this case, it is preferably provided in the form of a hair bleaching or a hair dyeing kit comprising the hair cosmetic of the present invention and a hair bleach or an oxidative hair dye. When the hair cosmetic of the present invention is used together with a hair bleach or an oxidative hair dye, it can be considered that the action of swelling the hair of the alkali agent contained in the hair bleach or the oxidative hair dye allows the components contained in the hair cosmetic of the present invention to penetrate deeper into the hair, which contributes to further improving the manageability and feel of the hair. Examples of the dosage form of the hair cosmetic of the present invention include a pump spray, an aerosol spray, a pumped foam, an aerosol foam, a gel, and a lotion.

When the hair cosmetic of the present invention is used together with a hair bleach or an oxidative hair dye, both may be mixed upon application and applied to the hair, but it is preferable to apply each separately to the hair. In that case, the hair cosmetic of the present invention may be applied to the hair before using the hair bleach or the oxidative hair dye, it may be applied to the hair after using the hair bleach or the oxidative hair dye, or both. In particular, it is preferable to apply it to the hair before using the hair bleach or the oxidative hair dye, that is, to use it as a pretreatment agent for the hair bleach or oxidative hair dye from the viewpoint of mitigating frizzy hair, reducing poofy hair, and further improving the manageability and feel of the hair.

[Hair Bleaching or Hair Dyeing Method]

The hair bleaching or hair dyeing method of the present invention includes the following steps (i) and (ii):
 (i) a step of applying the hair cosmetic of the present invention to the hair
 (ii) a step of applying a mixture of a first part containing an alkali agent and a second part containing an oxidizing agent of a hair bleach or an oxidative hair dye to the hair after the step (i)

<Step (i)>

The step (i) is performed by the method described in the above "Method of use".

<Step (ii)>

The step (ii) is a bleaching or hair dyeing treatment of applying to the hair a mixture of the first part and the second part of a hair bleach or an oxidative hair dye (hereinafter, simply referred to as "bleach or hair dye mixture"), and is performed in the same manner as a bleaching or hair dyeing treatment with a general hair bleach or oxidative hair dye.

The temperature at which the bleach or hair dye mixture is applied to the hair in the step (ii) is preferably from 15 to 45° C., and the amount of bleach or hair dye mixture to apply to the hair is, in terms of bath ratio to the mass of hair (mass of bleach or hair dye mixture/mass of hair), preferably 0.1 or more, more preferably 0.3 or more, still more preferably 0.5 or more, and preferably 5.0 or less, more preferably 3.0 or less, still more preferably 2.0 or less.

The mass ratio of the amount of hair cosmetic to apply to the hair in the step (i) to the amount of bleach or hair dye mixture to apply to the hair in the step (ii) (hair cosmetic/bleach or hair dye mixture) is preferably 0.02 or more, more preferably 0.1 or more, still more preferably 0.2 or more, and preferably 15 or less, more preferably 10 or less, still more preferably 5.0 or less, from the viewpoint of further improving the manageability and feel of the hair.

After applying the bleach or hair dye mixture to the hair, it is preferable to leave it on the hair for a certain period of time. The leaving time is preferably 1 minute or more, more preferably 5 minutes or more, and preferably 60 minutes or less, more preferably 45 minutes or less, still more preferably 30 minutes or less. After leaving, the bleach or hair dye mixture on the hair can be rinsed with water, and the hair can be optionally shampooed and dried.

Note that not only using the hair cosmetic of the present invention, but also using one containing only the component (C), or one containing the components (C) and (B) as the hair cosmetic used before applying the hair bleach or the oxidative hair dye to the hair is effective in mitigating frizzy hair, reducing poofy hair, and improving the manageability and feel of the hair. That is, a hair cosmetic containing the component (C), or a hair cosmetic containing the components (C) and (B) can also be used as the hair cosmetic to be used in the hair bleaching or hair dyeing kit, the pretreatment agent for the hair bleach or the oxidative hair dye, and the hair bleaching or hair dyeing method.

The preferred embodiments of the present invention will be further disclosed below with respect to the embodiments described above.

<1> A hair cosmetic containing the following components (A) and (B), wherein the mass ratio of the component (B) to the component (A), (B)/(A), is 0.25 or more and 1.90 or less:
 (A) an aromatic sulfonic acid or a salt thereof having a molecular weight of 300 or less; and
 (B) a cationic polymer having a cationic charge density of 3.3 meq/g or more and less than 4.5 meq/g.

<2> The hair cosmetic according to <1>, wherein the content of the component (A) is preferably 0.01 mass % or more, more preferably 0.05 mass % or more, still more preferably 0.10 mass % or more, still more preferably 0.20 mass % or more, still more preferably 0.50 mass % or more, still more preferably 0.70 mass % or more, still more preferably 0.80 mass % or more, still more preferably 0.9 mass % or more, and preferably 5 mass % or less, more preferably 3.0 mass % or less, still more preferably 2.0 mass % or less, still more preferably 1.8 mass % or less.

<3> The hair cosmetic according to <1> or <2>, wherein the content of the component (B) is preferably 0.10 mass % or more, more preferably 0.25 mass % or more, still more preferably 0.30 mass % or more, still more preferably 0.6 mass % or more, still more preferably 0.8 mass % or more, still more preferably 1.0 mass % or more, and preferably 20 mass % or less, more preferably 10 mass % or less, still more preferably 5 mass % or less, still more preferably 3.0 mass % or less, still more preferably 2.5 mass % or less, still more preferably 2.0 mass % or less, still more preferably 1.9 mass % or less.

<4> The hair cosmetic according to any one of <1> to <3>, wherein the mass ratio of the component (B) to the component (A), (B)/(A), is preferably 0.30 or more, more preferably 0.50 or more, still more preferably 0.55 or more, still more preferably 0.60 or more, still more preferably 0.8 or more, still more preferably 1.0 or more, and preferably 1.85 or less, more preferably 1.8 or less.

<5> A hair cosmetic containing the following components (A) and (B), wherein the mass ratio of the component (B) to the component (A), (B)/(A), is 0.25 or more and 1.90 or less:
 (A) an aromatic sulfonic acid or a salt thereof having a molecular weight of 300 or less at 0.5 mass % or more and 3.0 mass % or less; and
 (B) a cationic polymer having a cationic charge density of 3.3 meq/g or more and less than 4.5 meq/g at 0.2 mass % or more and 2.5 mass % or less.

<6> A hair cosmetic containing the following components (A) and (B), wherein the mass ratio of the component (B) to the component (A), (B)/(A), is 0.55 or more and 1.85 or less:
 (A) an aromatic sulfonic acid or a salt thereof having a molecular weight of 300 or less at 0.7 mass % or more and 2.0 mass % or less; and
 (B) a cationic polymer having a cationic charge density of 3.3 meq/g or more and less than 4.5 meq/g at 0.6 mass % or more and 2.0 mass % or less.

<7> The hair cosmetic according to any one of <1> to <6>, wherein the component (A) is preferably at least one selected from the group consisting of p-toluenesulfonic acid, xylenesulfonic acid, 2-naphthalenesulfonic acid (β-naphthalenesulfonic acid), 1-naphthalenesulfonic acid (α-naphthalenesulfonic acid), and the salts thereof, and more preferably one or more selected from the group consisting of p-toluenesulfonic acid and the salts thereof.

<8> The hair cosmetic according to any one of <1> to <7>, wherein the component (B) is preferably one or more selected from the group consisting of N-methylvinylimidazolinium/vinylpyrrolidone copolymer and acrylamide/acrylic acid/dimethyldiallylammonium chloride copolymer solution, and more preferably N-methylvinylimidazolinium/vinylpyrrolidone copolymer.

<9> The hair cosmetic according to any one of <1> to <8>, wherein the cationic charge density of the component (B) is preferably 3.4 meq/g or more, more preferably 3.45 meq/g or more, still more preferably 3.5 meq/g or more, and preferably 4.0 meq/g or less, more preferably 3.7 meq/g or less.

<10> The hair cosmetic according to any one of <1> to <9>, preferably further containing the following component (C):

(C) a compound of the following formula (4) or salt thereof:

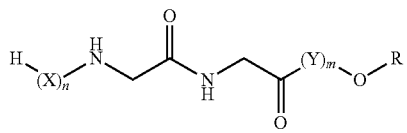

(4)

wherein X represents a divalent hydrocarbon group having 1 to 4 carbon atoms optionally substituted with a hydroxy group, or an amino acid residue, and Y represents an amino acid residue or a divalent group of the following chemical formula (5):

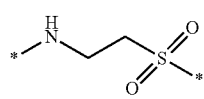

(5)

(wherein -* represents a bond which binds to an adjacent carbonyl group or oxygen atom.), R represents a monovalent hydrocarbon group having 1 to 4 carbon atoms optionally substituted with a hydrogen atom or a hydroxy group, and m and n represent 0 or 1. However, when m and n are 1 at the same time, X is not an amino acid residue.

<11> The hair cosmetic according to any one of <1> to <10>, which is preferably a hair treatment.

<12> The hair cosmetic according to any one of <1> to <11>, which is preferably a hair bleach or oxidative hair dye pretreatment agent used before applying to the hair a hair bleach or an oxidative hair dye comprising a first part containing an alkali agent and a second part containing an oxidizing agent.

<13> A hair bleaching or hair dyeing kit, comprising the hair cosmetic according to any one of <1> to <11>, and a hair bleach or an oxidative hair dye comprising a first part containing an alkali agent and a second part containing an oxidizing agent.

<14> The hair bleaching or hair dyeing kit according to <13>, wherein the hair cosmetic is preferably used before applying to the hair the hair bleach or the oxidative hair dye.

<15> Use of the hair cosmetic according to any one of <1> to <11> as a pretreatment agent for a hair bleach or an oxidative hair dye comprising a first part containing an alkali agent and a second part containing an oxidizing agent.

<16> A method for bleaching or dyeing hair, including the following steps (i) and (ii):
(i) a step of applying the hair cosmetic according to any one of <1> to <11> to the hair; and
(ii) a step of applying a mixture of a first part containing an alkali agent and a second part containing an oxidizing agent of a hair bleach or an oxidative hair dye to the hair after the step (i)

<17> A method for bleaching or dyeing hair, including a step of applying to the hair the hair cosmetic according to any one of <1> to <11>, and a mixture of a first part for a hair bleach or an oxidative hair dye containing an alkali agent, and a second part for a hair bleach or an oxidative hair dye containing an oxidizing agent.

<18> A method for bleaching or dyeing hair, including the following steps (i) and (ii):
(i) a step of applying to the hair a mixture of a first part containing an alkali agent and a second part containing an oxidizing agent of a hair bleach or an oxidative hair dye; and
(ii) a step of applying to the hair the hair cosmetic according to any one of <1> to <11> after the step (i)

EXAMPLES

Examples 1 to 8 and Comparative Examples 1 to 4

The treatment agents of the formulations shown in Table 1 were prepared, and their performance was evaluated by the following method. The results of these evaluations are also shown in the table.

<Hair Treating Method>
(i) A Japanese woman's hairs (hair of the same person which is slightly kinky and is slightly thicker than the average hair) were arranged at a width of about 5 mm, the upper ends were fixed, and tresses of a length from about 25 to 30 cm and a weight of 0.2 g were prepared. These tresses were washed with a cleansing shampoo of the following composition, and the hair shapes were photographed after fixing the upper ends and hanging them to dry. The tresses used in the Examples and Comparative Examples had a width within the range from 2.8 to 5.8 cm and a length within the range from 25 to 28.5 cm after the above drying. Note that the width refers to the size of the widest part when the tress is hung.

(ii) Next, the same hair was coated with each of the treatment agents described in Tables 1 to 3 to obtain a bath ratio of 1:1, and after 5 minutes at 30° C., was treated with running water for 30 seconds, then washed with shampoo and treated with a conditioner. Then, with the upper end of the hair fixed, they were blow-dried by hand while blowing warm air with a dryer, and the state of the hair after drying was photographed.

(iii) Finally, in order to verify the durability of the effect, the same hair was washed 7 times with shampoo, then with the upper end of the hair fixed, blow-dried by hand while blowing warm air with a dryer, and the state of the hair after drying was photographed.

The hairs after the treatments (i) to (iii) were used as the hair states "before treatment", "immediately after treatment", and "after washing 7 times with shampoo", respectively. In addition, all the hairs used were of the same person. In addition, the photographs were taken by photographing the entire hair with a camera from a distance of about 45 cm with the upper end of the hair fixed and hanging. Here, a record was kept so that the positions of the hair and the camera before the treatment, immediately after the treatment, and after 7 shampoos were all the same.

<Cleansing Shampoo Composition> (Composition is as is)
Sodium lauryl sulfate (EMAL 227, Kao Corporation): 57.00 mass %
Lauramide DEA (Aminon L-02, Kao Corporation): 1.50 mass %
Sodium benzoate (Aqueous sodium benzoate solution 35%, Aioi ChemiScience): 1.40 mass %
Disodium EDTA (Clewat N, Nagase ChemteX): 0.30 mass %

Phosphoric acid (food additive grade phosphoric acid 75%, Nippon Chemical Industrial Co., Ltd.): 0.02 mass %

Purified Water: 39.78 mass %

Method for Evaluating Manageability

The manageability was evaluated by comparing the degree of spread of the wisps after each treatment based on the photographed images. Specifically, the width of the wisps after each treatment was measured, and the rate of change in the width immediately after the treatment and after washing with shampoo 7 times was calculated based on the width of the hair before treatment as 1. A smaller rate of change indicates that the spread of the wisp was suppressed, and indicates that frizz was mitigated and that the manageability effect is high. In addition, a rate of change that is maintained small until after 7 shampoos indicates a high durability of the effect.

a hair dyeing treatment by the two-part oxidative hair dye shown in Table 3 according to the following hair treating method, it is possible to reduce frizzy and poofy hair, improve the manageability of hair, and maintain the effect for a certain period of time by a single treatment after the hair treatment.

<Hair Treating Method>

(i) A Japanese woman's hairs (hair of the same person which is slightly kinky and is slightly thicker than the average hair) were arranged at a width of about 5 mm, and tresses of a length from about 25 to 30 cm and a weight of 0.2 g were prepared, then these tresses were washed with the cleansing shampoo.

(ii) Next, the oxidative hair dye pretreatment agent shown in Table 2 was applied to the same hair to obtain a bath ratio (mass of oxidative hair dye pretreatment agent/mass of hair) of 0.22, and then the first part and the second part of the

TABLE 1

| | | | Example | | | | | |
|---|---|---|---|---|---|---|---|---|
| (Mass %: As is) | | | 1 | 2 | 3 | 4 | 5 | 6 |
| Formulation | (A) | p-Toluenesulfonic acid[*1] | 1.60 | 1.60 | 1.60 | 1.60 | 2.68 | 1.28 |
| | (B) | Polyquaternium-16[*2] | 1.50 | 2.50 | 5.00 | 9.00 | 5.00 | 5.00 |
| | | Polyquaternium-39[*3] | — | — | — | — | — | — |
| | (B') | Polyquaternium-7[*4] | — | — | — | — | — | — |
| | | Polyquaternium-47[*5] | — | — | — | — | — | — |
| | Others | 95% Ethanol | 10.00 | 10.00 | 10.00 | 10.00 | 10.00 | 10.00 |
| | | Methylparaben | 0.10 | 0.10 | 0.10 | 0.10 | 0.10 | 0.10 |
| | | 48% Sodium Hydroxide | 0.11 | 0.11 | 0.11 | 0.11 | 0.11 | 0.11 |
| | | Purified Water | Balance | Balance | Balance | Balance | Balance | Balance |
| | | Total | 100.00 | 100.00 | 100.00 | 100.00 | 100.00 | 100.00 |
| Effective Amount | | Component (A) (Mass %) | 1.00 | 1.00 | 1.00 | 1.00 | 1.68 | 0.80 |
| | | Component (B) (Mass %) | 0.30 | 0.50 | 1.00 | 1.80 | 1.00 | 1.00 |
| | | Mass Ratio (B)/(A) or (B')/(A) | 0.30 | 0.50 | 1.00 | 1.80 | 0.60 | 1.25 |
| Evaluation | Hair Manageability Effect | Immediately after treatment | 0.82 | 0.86 | 0.47 | 0.43 | 0.50 | 0.52 |
| | | After 7 shampoos | 0.82 | 0.82 | 0.53 | 0.35 | 0.50 | 0.62 |

| | | | Example | | Comparative Example | | | |
|---|---|---|---|---|---|---|---|---|
| (Mass %: As is) | | | 7 | 8 | 1 | 2 | 3 | 4 |
| Formulation | (A) | p-Toluenesulfonic acid[*1] | 0.94 | 1.60 | 1.60 | 1.60 | 1.60 | 1.60 |
| | (B) | Polyquaternium-16[*2] | 5.00 | — | 1.00 | 10.00 | — | — |
| | | Polyquaternium-39[*3] | — | 10.10 | — | — | — | — |
| | (B') | Polyquaternium-7[*4] | — | — | — | — | 11.11 | — |
| | | Polyquaternium-47[*5] | — | — | — | — | — | 4.80 |
| | Others | 95% Ethanol | 10.00 | 10.00 | 10.00 | 10.00 | 10.00 | 10.00 |
| | | Methylparaben | 0.10 | 0.10 | 0.10 | 0.10 | 0.10 | 0.10 |
| | | 48% Sodium Hydroxide | 0.11 | 0.11 | 0.11 | 0.11 | 0.11 | 0.11 |
| | | Purified Water | Balance | Balance | Balance | Balance | Balance | Balance |
| | | Total | 100.00 | 100.00 | 100.00 | 100.00 | 100.00 | 100.00 |
| Effective Amount | | Component (A) (Mass %) | 0.59 | 1.00 | 1.00 | 1.00 | 1.00 | 1.00 |
| | | Component (B) (Mass %) | 1.00 | 1.00 | 0.20 | 2.00 | 1.00 | 1.00 |
| | | Mass Ratio (B)/(A) or (B')/(A) | 1.70 | 1.00 | 0.20 | 2.00 | 1.00 | 1.00 |
| Evaluation | Hair Manageability Effect | Immediately after treatment | 0.90 | 0.77 | 0.95 | 0.91 | 1.00 | 1.28 |
| | | After 7 shampoos | 0.90 | 1.00 | 1.10 | 1.00 | 1.00 | 1.33 |

[*1] p-Toluenesulfonic acid (manufactured by Konan Chemical Manufacturing, effective amount: 62.6 mass %)
[*2] Luviquat Style (manufactured by BASF, charge density: 3.57 meq/g, effective amount: 25 mass %)
[*3] Merquat PLUS 3330 (manufactured by Lubrizol Advanced Materials, cationic charge density: 3.41 meq/g, effective amount: 20 mass %)
[*4] Merquat 550 (manufactured by Lubrizol Advanced Materials, cationic charge density: 3.05 meq/g, effective amount: 9.0 mass %)
[*5] Merquat 2001 (manufactured by Lubrizol Advanced Materials, cationic charge density: 3.21 meq/g, effective amount: 20.8 mass %)

Example 9 (Oxidative Hair Dye Pretreatment Agent)

Hereinafter, the aspects of the hair cosmetic of the present invention as an oxidative hair dye pretreatment agent are shown. By performing a hair treatment by the oxidative hair dye pretreatment agent shown in Table 2 before performing two-part oxidative hair dye described in Table 3 were mixed at a mass ratio of 1:1. The amount at which (application amount of oxidative hair dye pretreatment agent)/(application amount of hair dye mixture) is 0.22 was applied to the hair and left at 30° C. for 20 minutes.

Then, the hair was treated with running water for 30 seconds, washed with shampoo, and treated with a conditioner. After this, the hair was blow-dried by hand while blowing warm air with a dryer.

TABLE 2

| Oxidative Hair Dye Pretreatment Agent (Component) | (Mass %: As is) |
|---|---|
| p-Toluenesulfonic acid(*1) | 1.60 |
| Polyquaternium-16(*2) | 9.00 |
| Glycylglycine(*6) | 1.20 |
| 95% Ethanol | 10.00 |
| Methylparaben | 0.10 |
| 48% Sodium Hydroxide | 0.11 |
| Purified Water | 77.99 |
| | 100.00 |

(*1)p-Toluenesulfonic acid (manufactured by Konan Chemical Manufacturing, effective amount: 62.6 mass %)
(*2)Luviquat Style (manufactured by BASF, charge density: 3.57 meq/g, effective amount: 25 mass %)
(*6)Glycylglycine (manufactured by Yoneyama Yakuhin Kogyo)

TABLE 3

| | (Mass %) |
|---|---|
| First Part (Component) | |
| m-Aminophenol | 0.1 |
| Toluene-2,5-diamine | 1.0 |
| Resorcinol | 0.5 |
| EDTA-4Na | 0.1 |
| Ascorbic Acid | 0.4 |
| Anhydrous Sodium Sulfite | 0.3 |
| Monoethanolamine | 3.0 |
| 28% Ammonia Water | 2.0 |
| Water | 92.6 |
| | 100.0 |
| Second Part (Component) | |
| 35% Hydrogen Peroxide | 16.29 |
| Steartrimonium Chloride(*7) | 2.23 |
| Octyldodeceth-20(*8) | 1.08 |
| Ceteth-40(*9) | 0.75 |
| Ceteth-2(*10) | 0.33 |
| Stearyl Alcohol | 5.8 |
| Behenyl Alcohol | 1.66 |
| Liquid Paraffin(*11) | 10.17 |
| Concentrated Glycerin | 3.0 |
| Lanolin Fatty Acid(*12) | 0.01 |
| 8-Quinolinol Sulfate(*13) | 0.04 |
| 60% Etidronic Acid Aqueous Solution(*14) | 0.08 |
| 48% Sodium Hydroxide | 0.04 |
| Water | 58.52 |
| | 100.00 |

(*7)QUARTAMIN 86W (manufactured by Kao Corporation)
(*8)EMULGEN 2020G (manufactured by Kao Corporation)
(*9)NIKKOL BC-40TX (manufactured by Nippon Surfactant Industries
(*10)NIKKOL BC-2 (manufactured by Nippon Surfactant Industries)
(*11)HICALL K-350 (manufactured by Kaneda)
(*12)18 MEA-SO-(RB) (manufactured by Croda Europe)
(*13)8-Quinolinol Sulfate (manufactured by Nippon Rika)
(*14)Dequest 2010CS (manufactured by Italmatch Japan)

The invention claimed is:

1. A hair cosmetic comprising the following components (A) and (B), wherein a mass ratio of the component (B) to the component (A), (B)/(A), is 0.60 or more and 1.90 or less:
   (A) an aromatic sulfonic acid or a salt thereof having a molecular weight of 300 or less; and
   (B) a cationic polymer having a cationic charge density of 3.5 meq/g or more and 4.0 meq/g or less.

2. The hair cosmetic according to claim 1, wherein the mass ratio of the component (B) to the component (A), (B)/(A), is 0.60 or more and 1.85 or less.

3. The hair cosmetic according to claim 1, wherein the cationic charge density of the component (B) is 3.5 meq/g or more and less than 4.0 meq/g.

4. The hair cosmetic according to claim 1, wherein a content of the component (A) is 0.01 mass % or more and 5 mass % or less.

5. The hair cosmetic according to claim 4, wherein the content of the component (A) is 0.80 mass % or more and 5 mass % or less.

6. The hair cosmetic according to claim 1, wherein the component (A) is at least one selected from the group consisting of p-toluenesulfonic acid, xylenesulfonic acid, 2-naphthalenesulfonic acid (β-naphthalenesulfonic acid), 1-naphthalenesulfonic acid (α-naphthalenesulfonic acid), and the salts thereof.

7. The hair cosmetic according to claim 1, wherein a content of the component (B) is 0.10 mass % or more and 20 mass % or less.

8. The hair cosmetic according to claim 1, wherein the component (B) is one or more selected from the group consisting of N-methylvinylimidazolinium/vinylpyrrolidone copolymer and acrylamide/acrylic acid/dimethyldiallylammonium chloride copolymer solution.

9. The hair cosmetic according to claim 1, wherein the cationic charge density of the component (B) is 3.4 meq/g or more and 3.7 meq/g or less.

10. The hair cosmetic according to claim 1, further comprising the following component (C):
    (C) a compound of the following formula (4) or a salt thereof:

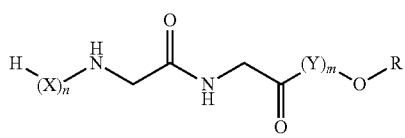

wherein X represents a divalent hydrocarbon group having 1 to 4 carbon atoms optionally substituted with a hydroxy group, or an amino acid residue, and Y represents an amino acid residue or a divalent group of the following chemical formula (5):

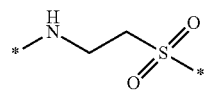

wherein -* represents a bond which binds to an adjacent carbonyl group or oxygen atom, R represents a monovalent hydrocarbon group having 1 to 4 carbon atoms optionally substituted with a hydrogen atom or a hydroxy group, and m and n represent 0 or 1, provided that when m and n are 1 at the same time, X is not an amino acid residue.

11. The hair cosmetic according to claim 1, which is a hair treatment.

12. The hair cosmetic according to claim 1, which is a hair bleach or an oxidative hair dye pretreatment agent used before applying to the hair a hair bleach or an oxidative hair dye comprising a first part containing an alkali agent and a second part containing an oxidizing agent.

13. A hair bleaching or hair dyeing kit, which is composed of
- the hair cosmetic according to claim 1, and
- a hair bleach or an oxidative hair dye comprising a first part containing an alkali agent and a second part containing an oxidizing agent.

14. The hair bleaching or hair dyeing kit according to claim 13, wherein the hair cosmetic is used before applying to the hair the hair bleach or the oxidative hair dye.

15. A method for bleaching or dyeing hair, the method comprising the following (i) and (ii):
  (i) applying the hair cosmetic according to claim 1 to the hair; and
  (ii) applying a mixture of a first part containing an alkali agent and a second part containing an oxidizing agent of a hair bleach or an oxidative hair dye to the hair after the applying (i).

16. A method for bleaching or dyeing hair, the method comprising applying to the hair
  the hair cosmetic according to claim 1, and
  a mixture of a first part for a hair bleach or an oxidative hair dye containing an alkali agent, and a second part for a hair bleach or an oxidative hair dye containing an oxidizing agent.

17. A method for bleaching or dyeing hair, the method comprising the following (i) and (ii):
  (i) applying to the hair a mixture of a first part containing an alkali agent and a second part containing an oxidizing agent of a hair bleach or an oxidative hair dye; and
  (ii) applying to the hair the hair cosmetic according to claim 1 after the applying (i).

* * * * *